(12) United States Patent
Wichert et al.

(10) Patent No.: US 6,890,889 B1
(45) Date of Patent: May 10, 2005

(54) MESOTRIONE FORMULATIONS

(75) Inventors: Rex Alan Wichert, Greensboro, NC (US); Thomas Homer Beckett, Greensboro, NC (US)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/363,014

(22) PCT Filed: Sep. 4, 2001

(86) PCT No.: PCT/IB01/01894

§ 371 (c)(1),
(2), (4) Date: Aug. 25, 2003

(87) PCT Pub. No.: WO02/019823

PCT Pub. Date: Mar. 14, 2003

Related U.S. Application Data

(60) Provisional application No. 60/231,796, filed on Sep. 11, 2000, and provisional application No. 60/231,007, filed on Sep. 8, 2000.

(51) Int. Cl.$^7$ ............... A01N 35/06; A01N 41/10
(52) U.S. Cl. .................................... 504/348
(58) Field of Search ........................ 504/348

(56) References Cited

U.S. PATENT DOCUMENTS 4,966,728 A * 10/1990 Hazen ................. 504/363

FOREIGN PATENT DOCUMENTS

| WO | 9219107 | 11/1992 |
| WO | 9517094 | 6/1995 |
| WO | 9748276 | 12/1997 |
| WO | 9963823 | 12/1999 |
| WO | 0030447 | 6/2000 |

OTHER PUBLICATIONS

Anderson. Weed Science: Principles and Applications. 3rd Ed. Chapter 16, "Cyclohexanedione Herbicides". West Pub. Co. p. 181–183. 1996.*

T.H. Beckett et al.: "Mesotrione–Postemergence Performance in Weed Control Programs in the Midwest", Proc. North Cent. Weed Sci. Soc., vol. 54, 1999, p. 95.

T.H. Beckett et al.: "ZA1296: A Versatile Postemergence Broadleaf Herbicide for Corn", Abstr. Meet. Weed Sci. Soc. AM., vol. 39, 1999, pp. 65–66.

B.G. Young et al.: "Optimizing Foliar Activity of Isoxaflutole on Giant Foxtail With Various Adjuvants", Pro. North Cent. Weed Sci. Soc., vol. 52, 1997, pp. 104–105.

* cited by examiner

*Primary Examiner*—S. Mark Clardy
(74) *Attorney, Agent, or Firm*—Rose M. Allen

(57) ABSTRACT

Herbicidal formulations comprising (A) mesotrione (2-[4-methylsulfonyl-2-nitrobenzoyl]-1,3-cyclohexanedione). (B) about 0.3 to about 2.5 percent of crop oil concentrate or about 0.3 to about 2.5 percent of methylated seed oil, on a volume to volume basis, based on the total of (A), (B), (C) and (D). (C) about 0.5 to about 5% of a urea ammonium nitrate on a volume to volume basis, based on the total of (A), (B), (C) and (D), or about 0.5 to 5% based on dry weight, of ammonium sulphate fertilizer, based on the total weight of (A), (B), (C) and (D), and (D) a diluent.

11 Claims, No Drawings

MESOTRIONE FORMULATIONS

This application claims benefit of Ser. No. 60/231,007 filed Sep. 8, 2000 and Ser. No. 60/231,796 filed Sep. 11, 2000.

Mesotrione, (2-[4-methylsulfonyl-2-nitrobenzoyl]-1,3-cyclohexane dione), is a new broadleaf weed herbicide being developed for post emergence and preemergence use in corn. Adjuvants are highly preferred in order to optimise its post emergence activity. Glasshouse and field experiments have been conducted to evaluate weed and crop response to mesotrione applied post emergence with several adjuvant systems. Rates of mesotrione ranged from 50 to 140 g active ingredient (ai) per acre (A). Adjuvant systems tested include;
(i) no adjuvant (control),
(ii) crop oil concentrate (COC),
(iii) non-ionic surfactant (NIS), and
(iv) methylated seed oil (MSO),
each with and without urea ammonium nitrate (UAN and ammonium sulphate (AMS) fertilizers.

The average crop response to mesotrione applied with crop oil concentrate plus ammonium nitrate or ammonium sulphate at 105 g active ingredient per hectare (ha) is less than 2% with a maximum injury of less than 10% in over 96% of the experiments.

The use of methylated seed oil with mesotrione increases the potential for crop injury. The average crop response to mesotrione applied with MSO plus UAN or AMS at 105 g active ingredient per hectare (ha) was only 3%, but injury was greater than 15% in more than 15% of the trials. In a series of trials where broadleaf weed control was challenged by large difficult-to-control weeds, mesotrione applied with COC plus UAN or AMS and mesotrione applied with MSO plus UAN or AMS gave similar levels of control. Mesotrione applied with NIS plus UAN or AMS tended to give less control than the combinations with COC or MSO. Experiments also show that varying water quality and application volumes have little or no impact on the activity of mesotrione when applied at recommended rates with these adjuvant systems.

Data from these experiments show that in order to optimise weed control and minimize crop response with mesotrione, the preferred adjuvant system is COC plus UAN. However, if efficacy with acceptable sacrifice in crop damage is the desired result, mesotrione plus MSO and UAN or AMS is the formulation of choice.

Thus, in a first aspect, the present invention provides a herbicidal formulation comprising
(A) mesotrione (2-[4-methylsulfonyl-2-nitrobenzoyl]-1,3-cyclohexanedione),
(B) about 0.3 to about 2.5 percent of crop oil concentrate or about 0.3 to about 2.5 percent of methylated seed oil, on a volume to volume basis, based on the total of (A), (B), (C) and (D),
(C) about 0.5 to about 5% of a urea ammonium nitrate on a volume to volume basis, based on the total of (A), (B), (C) and (D), or about 0.5 to 5% based on dry weight, of ammonium sulphate fertilizer, based on the total weight of (A), (B), (C) and (D), and
(D) a diluent.

Preferably, the mesotrione is utilized in an amount of about 1 ounce (28 g) to 6 ounces (170 g) per acre; the amount utilized per 100 (US) gallons (380 liters) of solution would thus correspond to how many gallons of solution would be applied on a per acre basis. Such amounts would ordinarily vary from about 3 ounces (85 g) in 5 gallons (19 l) to about 3 ounces (85 g) in 30 gallons (114 l). In a typical formulation, based on a 100 gallon (380 l) sample of the formulation, about 3 ounces (85 g) of mesotrione will be utilized for post-emergent use, and about 5–6 ounces (142–170 g) for preemergent usage.

The term "crop oil concentrate" is a well known term in the herbicide art and denotes mixtures of petroleum oils and non-ionic surfactants, preferably containing at least about 79% by weight of petroleum oil. There are numerous commercially available crop oil concentrate products, including, for example AGRI-DEX, PENETRATOR, and PENETRATOR PLUS and from Helena Chemical Company, HER-BIMAX from UAP, ES CROP OIL PLUS from Gromark, and CROP OIL PLUS, from Wilfarm, (83% parafinic oil, 17% emulsifier surfactant). In addition, U.S. Pat. No. 5,238,604, incorporated herein by reference, describes certain adjuvant systems and crop oil concentrate products.

Preferred amounts of crop oil concentrate are 0.5 to 2%, most preferably about 1% on a volume to volume basis.

Methylated Seed Oil is also commercially available. Examples include DESTINY from Cenex, methylated seed oil from Loveland, methylated seed oil from Helena Chemical, METH OIL from Riverside, PERSIST from Precision, SCOIL from Agsco, SUNDANCE II from Rosens, SUNIT-2 from American Cyanamid and SUPERB from Wilfarm.

In addition, commercial versions of the methylated seed oil are also sold as combinations with either UAN or AMS, for example PERSIST PLUS and PERSIST EXTRA from Precision (MSO plus UAN) and DYNE-A-PAK, from Helena Chemical (MSO plus UAN).

Preferably, the methylated seed oil is utilized in an amount of about 0.5 to 2.0 percent, on a volume-to-volume basis with the mesotrione, more preferably about 1 percent.

Preferably, about 1 to 3%, more preferably 1 to 2% of urea ammonium nitrate fertilizer is used. Preferably about 0.5% to 2% of ammonium sulphate is used.

The diluent is generally comprised of water. It is also possible to use other additives, for example buffers, to control pH. pH buffer substances are substances known to the person skilled in the art. A pH buffer substance is a mixture of a weak acid with a virtually completely dissociated salt of this acid and/or a mixture of a weak base with a virtually completely dissociated salt of this base (see, for example, Rompps Chemie Lexikon (Rompp's Chemical Encyclopedia, 7th edition, volume 5, head word "Buffer"). The pH of the buffer hardly changes on addition of acids or bases.

Preferred buffer substances in the preferred pH range from about 4 to about 11 are, for example, buffers which contain the following ions; acetate, phosphate, borate, carbonate, citrate, diethylmalonate, nitrilo-trismethylenephosphate. Zwitterionic buffers, such as, for example, glycine buffer or 2-(N-morpholino) ethanesulfonic acid (MES) are also suitable. The buffer used generally depends on the pH range, for example phthalate is typically used at a pH range of about 3 to about 4, acetate is typically used at a pH range of about 4 to about 5.5, phosphate is typically used at a pH range of about 5.5 to about 75, and carbonate is typically used at a pH range of about 9 to about 10. A pH buffer acetate system is employed in concentrations such that the concentration in the formulation is about 0.1 to about 0.3 mol/l, preferentially about 0.15 to about 0.25 mol/l. A pH- buffering acetate system is actually built in the 'Mesotrione/Acetochlor Premix' formulation at the specified molar ranges. For each buffer system the molar range is different and system specific, however, based on the buffering strength at the working pH range.

Further examples of commercially available buffer agents and adjuvants include, but are not limited to BUFFER PS from Helena, which includes alkyl-p-arylpolyethoxyethanol phosphates and organic phosphoric acid, typically utilized at a concentration of about 0.5 to about 4 pt (about 0.24 to 1.9 l) per 100 gal (380l), BUFFER EXTRA STRENGTH from Helena, which includes a blend of alkylarylpolyethoxyethanol phosphates and organic phosphoric acids, typically utilized at a concentration of about 4 oz to about 2 pt (about 0.095 to 0.95 l) per 100 gal (380 l), BUFFERCIDE from Custom Chemicals, which includes phosphoric acid, typically utilized at a concentration of about 1 to about 2 pt (about 0.47 to 0.95 l) per 100 gal (380 l), AERODYNE and PENETRATOR PLUS.

The formulations can be applied via the air or ground using known techniques, typically 5–30 gallons (19–114 l) per acre (0.4 ha) by ground or 1–5 gallons (3.8–19 l) per acre (0.4 ha) by air.

The amounts and proportions of components (B) and (C) above are preferred embodiments. It is contemplated that a range of about 0.1 to 1.0% could be utilized in each case.

In a further aspect of the invention, there is provided a method for controlling the growth of undesirable vegetation such as weeds around the locus of a desired plant species such as corn, which comprises applying the above formulations to the locus of such vegetation. Examples of undesired vegetation are velvetleaf, redroot pigweed, common water hemp, Palmer amaranth, ivyleaf morning-glory, prickly sida, giant ragweed, common ragweed common cocklebur, Eastern black nightshade, common lambsquarters, Pennsylvania smartweed, common sunflower, jimsonweed, hemp sesbania, toothed spurge, common purslane, large crabgrass, yellow foxtail and kochia.

EXAMPLES

A series of trials was conducted to evaluate the effect or adjuvants on control of broadleaf weeds with mesotrione. This series included trials on planted weeds and indigenous weeds. Each trial was designed as a randomised complete block with 3 or more replications. Mesotrione was applied at 0.094 lb ai/A (105 g/ha, 3 oz/A,) with MSO and COC at 1% v/v with and without UAN at 1 to 2.5% v/v and AMS at 8.5 lb/100 gallons (about 1%) spray solution. Thirteen trials were conducted in 1999 in which 38 evaluations were made on broadleaved weeds including velvetleaf, redroot pigweed, common water hemp, Palmer amaranth, ivyleaf morning-glory, prickly sida, giant ragweed, common ragweed, common cocklebur, Eastern black nightshade, common lambsquarters, Pennsylvania smartweed, common sunflower, jimsonweed, hemp sesbania, toothed spurge, common purslane and kochia The high levels of control observed with all treatments in 20 out of 38 of these datasets tends to mask adjuvant effects (see Table 1).

TABLE 1

Effect of adjuvants on broadleaf weed control with mesotrione
TRIAL DATA: H-99-US77-52

| | "All" Broadleaves, 14–36 DAA, 38 datasets | |
|---|---|---|
| | Mean Weed Control % | # >90% Consistency |
| Mesotrione 0.094 lb + MSO | 73 | 20 |
| Mesotrione 0.094 lb + MSO + UAN 1% | 78 | 21 |
| Mesotrione 0.094 lb + MSO + UAN 2.5% | 79 | 23 |
| Mesotrione 0.094 lb + MSO + AMS | 82 | 22 |
| Mesotrione 0.094 lb + COC | 75 | 22 |
| Mesotrione 0.094 lb + COC + UAN 1% | 78 | 19 |
| Mesotrione 0.094 lb + COC + UAN 2.5% | 77 | 21 |
| Mesotrione 0.094 lb + COC + AMS | 75 | 20 |
| Mesotrione 0.094 lb + UAN 1% | 69 | 17 |
| Mesotrione 0.094 lb + UAN 2.5% | 71 | 22 |
| Mesotrione 0.094 lb + AMS | 69 | 19 |

All herbicide rates are in pounds of active ingredient per acre (lb ai/A). 0.094 lb/A is about 105 g/ha.

Adjuvant rates are 1% MSO, 1% COC, 1 and 2.5% UAN and 8.5 lb/100 gal (about 1%) AMS.

The best demonstration of potential adjuvant effects is to concentrate on trials that were conducted under conditions which were not favourable for herbicidal activity or on weeds which are difficult to control with mesotrione applied alone. Mesotrione applied with the combination Of COC or MSO plus UAN or AMS gave significantly better weed Control than when applied with just COC or MSO (See Table 2).

Adjuvants also impact corn injury. This is best demonstrated by looking at the frequency of injury observed across a large number of field trials conducted between 1996 and 1999. These trials were all designed as randomised complete blocks with at least 3 replications. Mesotrione was applied at 0.094 lb ai/A (105 g ai/ha) (3 oz/A) plus 1% v/v COC or MSO with and without UAN at 2.5% v/v or AMS at 8 to 17 lb/100 gallons (about 1–2%). Combinations of COC plus UAN or AMS result in fewer occurrences of crop injury than MSO plus UAN or AMS See Table 3).

TABLE 2

Effect of adjuvants from selected trials (adverse conditions (OH) and Difficult-to-control species (AMBEL and AMBTR))
TRIAL DATA; H-99-US77-52

| | *OH Velvetleaf ABUTH 28 DAA 6–8 leaf, 8–10" | *OH Common Ragweed AMBEL 28 DAA 12–14 leaf, 5.5–7" | WI Common Ragweed AMBEL 32 DAA 8–9 leaf, 8–9" | MN Giant Ragweed AMBTR 28 DAA 5 leaf, 2–6" | IN Giant Ragweed AMBTR 28 DAA 9–10 leaf, 8–11" | Average |
|---|---|---|---|---|---|---|
| Mesotrione 0.094 lb + MSO | 27 | 27 | 63 | 88 | 92 | 59 |
| Mesotrione 0.094 lb + MSO + UAN 1% | 73 | 80 | 83 | 93 | 99 | 86 |
| Mesotrione 0.094 lb + MSO + UAN 2.5% | 60 | 63 | 89 | 90 | 98 | 80 |
| Mesotrione 0.094 lb + MSO + AMS | 65 | 65 | 92 | 88 | 98 | 82 |
| Mesotrione 0.094 lb + COC | 47 | 57 | 71 | 68 | 92 | 67 |
| Mesotrione 0.094 lb + COC + UAN 1% | 70 | 73 | 81 | 83 | 80 | 77 |
| Mesotrione 0.094 lb + COC + UAN 2.5% | 60 | 60 | 91 | 94 | 89 | 79 |

TABLE 2-continued Effect of adjuvants from selected trials (adverse conditions (OH) and Difficult-to-control species (AMBEL and AMBTR))
TRIAL DATA; H-99-US77-52

|  | *OH Velvetleaf ABUTH 28 DAA 6–8 leaf, 8–10" | *OH Common Ragweed AMBEL 28 DAA 12–14 leaf, 5.5–7" | WI Common Ragweed AMBEL 32 DAA 8–9 leaf, 8–9" | MN Giant Ragweed AMBTR 28 DAA 5 leaf, 2–6" | IN Giant Ragweed AMBTR 28 DAA 9–10 leaf, 8–11" | Average |
|---|---|---|---|---|---|---|
| Mesotrione 0.094 lb + COC + AMS | 52 | 52 | 72 | 80 | 96 | 70 |
| Mesotrione 0.094 lb + UAN 1% | 23 | 27 | 65 | 72 | 82 | 54 |
| Mesotrione 0.094 lb + UAN 2.5% | 23 | 23 | 91 | 77 | 98 | 62 |
| Mesotrione 0.094 lb + AMS | 38 | 38 | 85 | 77 | 95 | 67 |
| 5% LSDs | 9 | 10 | 13 | 13 | 18 | |

*Drought conditions

All herbicide rates in pounds of active ingredient per acre (lbai/A).

Adjuvant rates are 1% MSO, 1% COC, 1 and 2.5% UAN and 8.5 lb/100 gallon (about 1%) AMS

TABLE 3

Effect of Adjuvant on Frequency of Corn Injury using 0.094 lb ai/A (105 g/ha) mesotrione with various adjuvants

| Adjuvant | mean | # trials | <5 | 5–10 | 10–15 | 15–20 | 20–25 | 25–30 | >30 |
|---|---|---|---|---|---|---|---|---|---|
| COC 1% | 0.6 | 60 | 98 | 2 | 0 | 0 | 0 | 0 | 0 |
| COC 1% + UAN 2.5% | 1.8 | 101 | 90 | 6 | 3 | 0 | 1 | 0 | 0 |
| COC 1% + AMS | 1.6 | 15 | 80 | 20 | 0 | 0 | 0 | 0 | 0 |
| MSO 1% | 0.6 | 29 | 100 | 0 | 0 | 0 | 0 | 0 | 0 |
| MSO 1% + UAN 2.5% | 3.0 | 38 | 76 | 11 | 5 | 8 | 0 | 0 | 0 |
| MSO 1% + AMS | 5.5 | 25 | 68 | 8 | 4 | 12 | 4 | 4 | 0 |

Examples of Preferred Formulations Based on 100 Gallons (379 l) of Formulated Solution for Typical 10 Gallon (38 l) per acre (0.4 ha) Application 1. (A) 30 ounces (1 kg) of (2-[4-methylsulfonyl-2-nitrobenzoyl]-1,3-cyclohexanedione),
   (B) 1 gallon (3.8 l) of crop oil concentrate,
   (C) 1.5 gallons (5.7 l) of urea ammonium nitrate, and
   (D) the balance water 2. (A) 30 ounces (1 kg) of (2-[4-methylsulfonyl-2-nitrobenzoyl]-1,3-cyclohexanedione),
   (B) 1 gallon (3.8 l) of methylated seed oil,
   (C) 17 lbs (7.7 Kg) of ammonium sulphate fertilizer, and
   (D) the balance water 3. (A) 30 ounces (1 kg) of (2-[4-methylsulfonyl-2-nitrobenzoyl]-1,3-cyclohexanedione),
   (B) 1 gallon (3.8 l) of crop oil concentrate,
   (C) 1.5 gallons (5.7 l) of urea ammonium nitrate, and
   (D) the balance water

We claim:
1. A herbicidal formulation comprising
   (A) mesotrione (2-[4-methylsulfonyl-2-nitrobenzoyl]-1,3-cyclohexanedione);
   (B) about 0.3 to about 2.5 percent of crop oil concentrate, or about 0.3 to about 2.5 percent of methylated seed oil, on a volume to volume basis, based on the total of (A), (B); (C) and (D),
   (C) about 0.5 to about 5% of a urea ammonium nitrate on a volume to volume basis, based on the total of (A), (B), (C) and (D), or about 0.5 to 5% based on dry weight, of ammonium sulphate fertilizer, based on the total weight of (A), (B), (C) and (D), and
   (D) a diluent.
2. The formulation of claim 1, comprising about 0.5 to 2.0% crop oil concentrate.
3. The formulation of claim 1, comprising about 1% crop oil concentrate.
4. The formulation of claim 1, comprising about 0.5 to 2.0% methylated seed oil.
5. The formulation of claim 1, comprising about 1% methylated seed oil.
6. The formulation of claim 1, comprising about 1 to 3% urea ammonium nitrate fertilizer.
7. The formulation of claim 1, comprising about 0.5 to 2% ammonium sulphate fertilizer.

8. A herbicidal formulation, on the basis of a 100 gallon solution, comprising
   (A) about 30 ounces of (2-[4-methylsulfonyl-2-nitrobenzoyl]-1,3-cyclohexanedione),
   (B) about 1 gallon of crop oil concentrate or 1 gallon of methylated seed oil or a blend thereof,
   (C) about 2 5 gallons of a urea ammonium nitrate on a volume to volume basis or about 17 lbs of ammonium sulphate fertilizer, and
   (D) the balance water.

9. A method for controlling the growth of undesired vegetation around the locus of a desired plant, which comprises applying the formulation of claim 1 to the locus of said vegetation.

10. The method of claim 9 in which the desired plant is corn.

11. The method of claim 10, wherein said undesired vegetation is selected form the group comprising velvetleaf, redroot pigweed, common waterhemp, Palmer amaranth, ivyleaf morningglory, prickly sida, giant ragweed, common ragweed, common cocklebur, Eastern black nightshade, common lambsquarters, Pennsylvania smartweed, common sunflower, jimsonweed, hemp sesbania, toothed spurge, common puslane, large crabgrass, yellow foxtail and Kochia.

* * * * *

UNITED STATES PATENT AND TRADEMARK OFFICE
CERTIFICATE OF CORRECTION

PATENT NO. : 6,890,889 B1 Page 1 of 1
DATED : May 10, 2005
INVENTOR(S) : Wichert et al.

It is certified that error appears in the above-identified patent and that said Letters Patent is hereby corrected as shown below:

Column 6,
Line 52, should read as follows: -- (C) about 0.5 to about 5% of a urea ammonium nitrate on --

Column 7,
Line 7, should read as follows: -- (C) about 2.5 gallons of a urea ammonium nitrate on a --

Signed and Sealed this

Twelfth Day of July, 2005

JON W. DUDAS
*Director of the United States Patent and Trademark Office*